(12) United States Patent
Liu

(10) Patent No.: US 11,331,516 B2
(45) Date of Patent: *May 17, 2022

(54) TREATMENT PLANNING METHOD AND RADIOTHERAPY SYSTEM

(71) Applicant: OUR UNITED CORPORATION, Xi'an (CN)

(72) Inventor: Haifeng Liu, Xi'an (CN)

(73) Assignee: OUR UNITED CORPORATION, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/039,033

(22) Filed: Sep. 30, 2020

(65) Prior Publication Data
US 2021/0038913 A1 Feb. 11, 2021

Related U.S. Application Data

(63) Continuation-in-part of application No. 15/979,490, filed on May 15, 2018, now Pat. No. 10,850,123, (Continued)

(51) Int. Cl.
*A61N 5/10* (2006.01)

(52) U.S. Cl.
CPC ......... *A61N 5/1031* (2013.01); *A61N 5/1045* (2013.01); *A61N 5/1081* (2013.01)

(58) Field of Classification Search
CPC .... A61N 5/103; A61N 5/1031; A61N 5/1045; A61N 5/1081; A61N 5/1037; A61N 5/1049; A61N 2005/1092; A61N 5/1042; A61N 5/1048; A61N 5/1017; A61N 2005/1091; A61N 2005/105; A61N 5/1067; A61N 5/1064; A61N 5/10; A61N 5/1001; A61N 5/1077; A61N 2005/1019; A61N 2005/1022; A61N 5/1027; A61B 34/30; A61B 6/506; A61B 2017/306; A61B 6/508; A61B 6/4458; A61B 6/583; A61B 6/032; A61B 6/06; A61B 6/4266; A61B 6/483; A61B 34/20; A61B 6/035; A61B 6/4429;
(Continued)

(56) References Cited

U.S. PATENT DOCUMENTS 5,291,404 A 3/1994 Kurokawa
5,430,308 A * 7/1995 Feichtner ............. G01N 23/043
250/580
(Continued)

*Primary Examiner* — Irakli Kiknadze
(74) *Attorney, Agent, or Firm* — Emerson, Thomson & Bennett, LLC; Roger D. Emerson; Warren A. Rosborough

(57) ABSTRACT

A method of making a treatment plan with a treatment planning system and radiotherapy system are provided. The method includes: acquiring a preset dose distribution scheme; generating at least one radiation dose distribution scheme to be used with the treatment planning system, wherein the treatment plan system is adapted to at least one of beam energy of the radiotherapy system, a size of a collimator of the radiotherapy system, a radiation angle and radiation time of the radiotherapy system; and comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan.

20 Claims, 10 Drawing Sheets

Related U.S. Application Data which is a continuation of application No. PCT/CN2015/094670, filed on Nov. 16, 2015.

(58) Field of Classification Search
CPC ... A61B 6/4435; A61B 6/4441; A61B 6/4452; A61B 6/481; A61B 6/482; A61B 6/488; A61B 6/50; G01N 33/0047; G01N 23/04; G01N 2223/316; G01N 23/20; G06F 11/2236; G06F 16/5866; G06F 2203/04806; G06F 3/0482; G06F 3/0484; G06F 3/04845; G06F 3/1204; G06T 2207/20072; G06T 2207/30004; G06T 2207/30241; G06T 7/0012; G06T 7/60; H05H 15/00; H05H 2007/004; H05H 2007/125; H05H 7/02; H05H 7/12; H05H 9/00; H04L 29/08; H04L 67/42; G01T 1/02; G01T 1/2928; G01T 1/2985; G01T 1/2914; G01T 1/22; G06N 3/02; G06N 3/08; G06N 5/022; G06N 20/10; G06N 7/005; G21K 1/046; G21K 1/093; G16H 50/20; G06K 9/3241; G06K 9/2054

USPC .................................................... 378/62, 65
See application file for complete search history.

(56) References Cited

U.S. PATENT DOCUMENTS

| 7,027,557 | B2 | 4/2006 | Llacer | |
| 7,804,935 | B2* | 9/2010 | Yin | A61N 5/1031 |
| | | | | 378/65 |
| 9,987,504 | B2* | 6/2018 | Nord | A61N 5/1071 |
| 10,265,543 | B2* | 4/2019 | Bharat | A61N 5/1071 |
| 10,850,123 | B2* | 12/2020 | Liu | A61N 5/1049 |
| 2003/0007601 | A1* | 1/2003 | Jaffray | A61B 6/508 |
| | | | | 378/65 |
| 2007/0086569 | A1 | 4/2007 | Johnsen | |
| 2009/0041188 | A1* | 2/2009 | Keall | A61N 5/1042 |
| | | | | 378/65 |
| 2010/0189376 | A1 | 7/2010 | Bertram | |
| 2011/0085643 | A1* | 4/2011 | Zhu | A61N 5/1031 |
| | | | | 378/65 |

\* cited by examiner

TREATMENT PLANNING METHOD AND RADIOTHERAPY SYSTEM

CROSS REFERENCE

The present application is a continuation-in-part of U.S. application Ser. No. 15/979,490 filed on May 15, 2018, and entitled "TREATMENT PLANNING METHOD, APPARATUS AND RADIOTHERAPY SYSTEM", which is a continuation of International Application No. PCT/CN2015/094670 filed on Nov. 16, 2015, and entitled "METHOD, DEVICE AND RADIOTHERAPY SYSTEM FOR MAKING TREATMENT PLAN". The entire disclosures of the prior applications are hereby incorporated by reference in their entirety.

TECHNICAL FIELD

This disclosure relates to the field of radiotherapy, in particular to a method and apparatus for treatment planning, and related radiotherapy system.

BACKGROUND

Directional radiosurgery (SRS) techniques, for example, gamma radiation employed cobalt-60 source, are often used in neurosurgery for tumors, vascular malformations, and similar malformations in the brain. In directional radiosurgery, it is preferable to distribute multiple radioactive sources around the patient's head, with the help of collimators to focus the beam of beams on a small, spherical region in the brain. The diameter of the sphere is selectable, and the duration time of radiation is adjustable (e.g. by weighting), and a radiation dose field in the brain can be achieved by superimposing doses from several irradiation points. It is expected that the largest dose is received by the tumor, while the surrounding tissue receives the smallest dose.

In order to achieve a high concentration of radiotherapy dose in the target region to be irradiated, the dose outside the target region is needed to be decreased to avoid harm to normal tissues. That is to say, it is very necessary to adjust the radiation dose in a radiosurgery process, to improve the treatment accuracy. Conformality and intensity modulation are two main technologies used in such radiotherapy equipment. And, it is also usually adopted approaches of changing the collimator aperture and/or changing the window shape of a multi-leaf grating, to achieve this goal. Taking a gamma knife as an example, several collimators with different apertures are used to achieve the purpose of adjusting the dose. However, continuous adjustment is not possible and the treatment accuracy is reduced. Taking a medical linear accelerator as another example, the dose is usually adjusted by changing the window shape of the multi-leaf grating. However, the structure of the multi-leaf grating is complicated, resulting in a high failure rate.

SUMMARY

In order to solve the above technical problems, a technical solution employed by the present disclosure is to provide a method of making a treatment plan with a treatment planning system. The treatment plan is applicable to a radiotherapy system. The method comprising: acquiring a preset dose distribution scheme; generating at least one radiation dose distribution scheme to be used with the treatment planning system, wherein the treatment plan system is adapted to at least one of beam energy of the radiotherapy system, a size of a collimator of the radiotherapy system, a radiation angle and radiation time of the radiotherapy system; and comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan. The treatment planning system includes a preset algorithm, the preset algorithm generates the at least one radiation dose distribution scheme to be used based on a function of $f(\Phi, \theta, B, D, t, d)$, wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

To solve the above technical problems, another technical solution employed by the present disclosure is to provide a radiotherapy system. The radiotherapy system comprises: at least one therapeutic head configured to generate a radiation beam; a treatment couch configured to define a position of a target region; a gantry configured to support the at least one therapeutic head, and move the therapeutic head relative to the treatment couch in multiple dimensions; and a treatment planning apparatus, the treatment planning apparatus including a processor, wherein the processor is configured with instructions to: acquire a preset dose distribution scheme; generate at least one radiation dose distribution scheme to be used, wherein the treatment plan is adapted to at least one of beam energy of the radiotherapy system, a size of a collimator of the radiotherapy system, a radiation angle and radiation time of the radiotherapy system; and compare the at least one radiation dose distribution scheme to be used with the preset dose distribution scheme, and determine, among the at least one radiation dose distribution scheme, a radiation dose distribution scheme that is the closest to the preset dose distribution scheme to make the treatment plan. The treatment planning apparatus includes a preset algorithm, the preset algorithm generates the at least one radiation dose distribution scheme to be used based on a function of $f(\Phi, \theta, B, D, t, d)$, wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

To solve the above technical problems, another technical solution employed by the present disclosure is to provide a method of making a treatment plan. The treatment plan is applicable to a radiotherapy system. The method comprising: acquiring a preset dose distribution scheme; generating a radiation dose distribution scheme to be used with a treatment planning system, wherein the treatment plan system is adapted to at least one of beam energy of the radiotherapy system, a size of a collimator of the radiotherapy system, a radiation angle and radiation time of the radiotherapy system such that a continuous change of radiation dose in a radiation region of the beam is formed with a specific spatial distribution; and comparing the radiation dose distribution scheme to be used with the preset dose distribution scheme, and determining a radiation dose distribution scheme that is the closest to the preset dose distribution scheme to make the treatment plan. The treatment planning system includes a preset algorithm, the preset algorithm generates the at least one radiation dose distribution scheme to be used based on a function of f($\Phi$, $\theta$, B, D, t, d), wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

According to the treatment planning method of the present disclosure, the therapeutic head is located at different radiation angles by utilizing the continuous movement of the therapeutic head (including rotation and swing movements, etc.), and the dose distribution of the therapeutic head is different at different radiation angles, so that the dose distribution schemes are adjustable by changing the radiation angle of therapeutic head(s). The adjusted dose distribution schemes are compared to the preset dose distribution scheme to obtain at least one radiation dose distribution scheme that is closest to the preset dose distribution scheme and further develops a treatment plan. As a result, the treatment planning accuracy is improved without changing the hardware configuration.

DETAILED DESCRIPTION

To describe the technical solutions in the embodiments of the present disclosure more clearly, the following briefly introduces the accompanying drawings required for describing the embodiments. The accompanying drawings in the following description show merely some embodiments of the present disclosure, and a person skilled in the art may still derive other drawings from these accompanying drawings.

The principle of the present disclosure is to fully utilize the superposition effect of radiation dose in four multiple dimensions of space and time to achieve a reasonable dose distribution. Taking a general flashlight beam as an example, a white paper is placed on the beam path to observe the light intensity and photometric distribution at a specific section, and a circular or substantially elliptical spot is observed on the paper. When changing the incident angle of the light beam, the shape of the light spot changes, and the light intensity (i.e. radiation energy per unit area) also changes. Similarly, using this principle, the radiation beams of the radioactive source(s) is controlled to perform radiation at a predetermined time from different angles, while being complemented by adjustment of the collimation size, thereby forming a continuous change of the radiation dose in a specific spatial region, and showing a specific spatial distribution.

Figure 1:
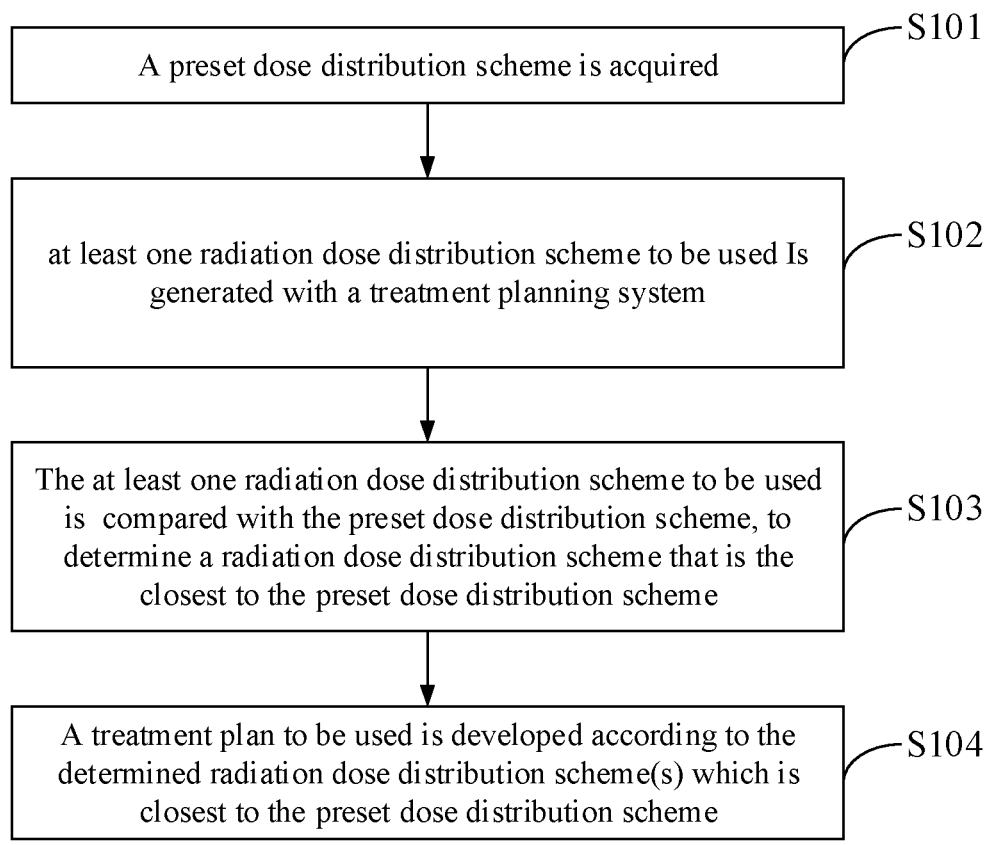
FIG. 1 is a flowchart of a method for treatment planning, according to an exemplary embodiment.

Referring to FIG. 1, the present disclosure provides a method for treatment planning, which includes the following steps.

In step S101, a preset dose distribution scheme is acquired.

For example, the preset dose distribution scheme may be acquired by a user inputting a preset dose distribution scheme. For further example, the preset dose distribution scheme is input according to a user's command. In some embodiments, a doctor may calculate the preset dose distribution scheme by semi-empirical model or Boltzmann transport equation according to the position of the target region to be irradiated. In this embodiment, the preset dose distribution scheme is about a confirmed target region and surrounding tissues, which are determined responding to a tumor and tissues surrounding the tumor. When it is necessary to perform treatment planning by a computer, the preset dose distribution scheme is stored in a computer system by a manual or automatic input apparatus.

In step S102, generating at least one radiation dose distribution scheme to be used with the treatment planning system. The treatment plan system is adapted to at least one of beam energy of the radiotherapy system, a size of a collimator of the radiotherapy system, a radiation angle and radiation time of the radiotherapy system.

In one exemplary embodiment, the treatment planning system may generate one or more radiation dose distribution scheme to be used by adapting at least one of: the radiation energy of a radiotherapy system, the size of each collimator of the radiotherapy system, a radiation angle and a radiation time of the radiotherapy system according to the preset algorithm, and, and wherein the radiation angle is continuously variable.

In another exemplary embodiment, the plurality of radiation dose distribution schemes may be a plurality of final dose distribution schemes same or close to the preset dose distribution scheme. The final dose distribution schemes each responds to a treatment plan, and each of the treatment plans is generated according to another preset algorithm and equipment parameters of the radiotherapy system. In the present embodiment, different treatment plans employ different parameters of radiation energy, radiation field, and radiation times, and also correspond to different radiation dose distribution schemes.

In the present embodiment, at least one therapeutic head is disposed on the radiotherapy system 100, and is capable of continuously moving in at least one dimension with respect to the target region to be irradiated, so that the radiation angle is continuously variable. Specifically, the radiotherapy system 100 may be any stereotactic radiosurgery (SRS) apparatus or stereotactic radiotherapy (SRT) apparatus, such as a 3-dimentional conformal radiotherapy (3D-CRT) equipment and intensity modulated radiotherapy (IMRT) equipment. The therapeutic head includes, at least, the parts of radioactive source and collimator. Exemplarily, the radioactive source may be cobalt-60 radioactive source with certain radiation energy, and the collimator may be aperture collimator or multi-leaf collimator. Of course, the radioactive source may also be an X-ray source, which is not limited in this disclosure.

Exemplarily, the preset algorithm includes a function of $f(\Phi, \theta, B, D, t, d)$, wherein the variable $\Phi$ represents a rotation angle of the therapeutic head rotated in a first dimension with respect to the target region, and the variable $\theta$ represents a swing angle that the therapeutic head swung relative to the target region in a second dimension. The second dimension is different from the first dimension. B is the radiation energy parameter, variable D represents a distance from the radioactive source emission point of the therapeutic head to the target region, the variable t is the radiation time, and the variable d is the radiation field parameters of the therapeutic head. Based on the function f, multiple dose distribution values are calculated. It should be noted that the variable $\Phi$ and the variable $\theta$ represent the irradiation angles of the therapeutic heads in different dimensions, respectively, and the different angles correspond to the dose distributions. Therefore, the determination of variables $\Phi$ and $\theta$ may be used to calculate the corresponding dose distributions. As such, since the dose distributions have been calculated, the dose distribution scheme to be used is determined based on the corresponding dose distributions.

The radiation field parameters are determined by the collimator(s). In the case where the collimator is an aperture collimator, the collimator includes a plurality of collimation holes, and the radiation field parameters are the sizes of the collimation holes. Or, in the case that the collimator is a multi-leaf collimator, the radiation field parameters may be related to a shaped region, e.g. the size parameters of the region, where the radiation beams passing through and shaped by blades or leaves. In this embodiment, the radiation field parameters are specifically determined by the number of blades of the multi-leaf collimator, the speed of blade movement, the position of the blades, and the like.

In step S103, the at least one radiation dose distribution scheme isrespectively compared with the preset dose distribution scheme, to determine at least one radiation dose distribution scheme closest to the preset dose distribution scheme.

In this embodiment, by comparing multiple calculated dose distribution values with the preset radiation dose distribution scheme, at least one dose distribution parameter closest to that of the preset radiation dose scheme is determined, and then the treatment plan is determined. The calculation of the dose distribution values would be specified in the following paragraphs.

Exemplarily, in an embodiment, the comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan comprises: comparing the at least one radiation dose distribution scheme to be used with the preset dose distribution scheme; when a difference between the at least one radiation dose distribution scheme to be used and the preset dose distribution scheme is greater than a safety threshold, adjusting a parameter of the treatment planning system to regenerate the at least one radiation dose distribution scheme to be used; comparing the at least one regenerated radiation dose distribution scheme to be used with the preset dose distribution scheme, and determining, among the at least one regenerated radiation dose distribution scheme, a radiation dose distribution scheme that is the closest to the preset dose distribution scheme to make the treatment plan.

Exemplarily, in an embodiment, the comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan comprises: comparing a difference between the at least one radiation dose distribution scheme to be used and the preset dose distribution scheme with a safety threshold, and determining a radiation dose distribution scheme to be used based on a result of the comparison to make the treatment plan. The safety threshold may be set by a physician according to his or her experience. No limitation is set to the safety threshold.

In step S104, a treatment plan to be used is developed according to the determined radiation dose distribution scheme(s) which is closest to the preset dose distribution scheme.

Exemplarily, a method of making a treatment plan is provided in an embodiment. The treatment plan is applicable to a radiotherapy system. The method comprising: acquiring a preset dose distribution scheme; generating a radiation dose distribution scheme to be used with a treatment planning system, wherein the treatment plan system is adapted to at least one of beam energy of the radiotherapy system, a size of a collimator of the radiotherapy system, a radiation angle and radiation time of the radiotherapy system such that a continuous change of radiation dose in a radiation region of the beam is formed with a specific spatial distribution; and comparing the radiation dose distribution scheme to be used with the preset dose distribution scheme, and determining a radiation dose distribution scheme that is the closest to the preset dose distribution scheme to make the treatment plan. The treatment planning system includes a preset algorithm, the preset algorithm generates the at least one radiation dose distribution scheme to be used based on a function of $f(\Phi, \theta, B, D, t, d)$, wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

Exemplarily, in an embodiment, the radiation region of the beam is generally where a tumor is located. Different radiation doses may be needed by different tumor areas with various degrees of tumor invasion. Thus, a continuous change of radiation doses in a radiation region of the beam is formed with a specific spatial distribution for treating different tumor areas with various degrees of tumor invasion.

According to the treatment planning method of the present disclosure as mentioned above, the therapeutic head 102 is located at different radiation angles by utilizing the continuous movements of the therapeutic head 102 (including rotation movement and swing movement, etc.), and the dose distribution of the therapeutic head is different at different radiation angles. As such, the dose distribution schemes are adjustable by changing the radiation angle of therapeutic head, so as the dose distribution schemes are compared with the preset dose distribution scheme, to obtain the radiation dose distribution scheme that is closest to the preset dose distribution scheme and further develops a final treatment plan. As a result, the treatment plan accuracy is improved.

Figure 2:
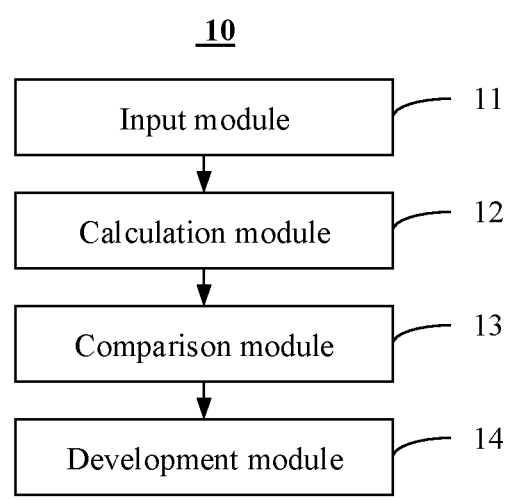
FIG. 2 is a functional block diagram of an apparatus for treatment planning, according to an exemplary embodiment.

The present disclosure also provides a treatment planning apparatus 10 comprising a processor for implementing the above-mentioned treatment planning method. Referring to FIG. 2, the processor of the treatment planning apparatus 10 is used to perform actions of the following modules, such as an input module 11, a calculation module 12, a comparison module 13, and a development module 14.

The input module 11 is configured to obtain the preset dose distribution scheme. In this embodiment, a doctor may calculate the preset dose distribution scheme by semi-empirical model or Boltzmann transport equation according to the position of the target region to be irradiated. When it is necessary to perform treatment planning by a computer, the preset dose distribution scheme is obtained by the input module 11 and stored in a computer system by a manual or automatic input apparatus.

The calculation module 12 is configured to generate a plurality of radiation dose distribution schemes according to a preset algorithm and equipment parameters of the radiotherapy system, wherein the equipment parameters of the radiotherapy system include one or more of the parameters of radiation energy, radiation field, radiation angles, dose distribution at different radiation angles, and radiation time, etc.

Exemplarily, the preset algorithm includes a function $f(\Phi, \theta, B, D, t, d)$, wherein the variable $\Phi$ represents a rotation angle of the therapeutic head rotated in a first dimension with respect to a target region, and the variable $\theta$ represents a swing angle that the therapeutic head swung relative to the target region in a second dimension. The second dimension is different from the first dimension. B is the radiation energy parameter, variable D represents the distance from the radioactive source emission point of the therapeutic head to the target region, and the variable t is the radiation time, the variable d is the radiation field parameters of the therapeutic head. Based on the function f, multiple dose distribution values are calculated.

It is understood that at least one variable in the above function $f(\Phi, \theta, B, D, t, d)$ may be zero. For example, in the case where the therapeutic head rotates only along the axis, the variable $\theta$ is zero.

The comparison module 13 is configured to compare each of the plurality of radiation dose distribution schemes with the preset dose distribution scheme, respectively, to confirm at least one radiation dose distribution scheme which is closest to the preset dose distribution scheme. In this embodiment, by comparing each of multiple calculated dose distribution values to that of the preset radiation dose distribution scheme, a dose distribution parameter closest to the preset radiation dose is determined, and then the radiation dose distribution scheme is determined to further determine the treatment plan.

The development module 14 is configured to develop or make a treatment plan to be executed, according to the determined radiation dose distribution scheme which is closest to the preset dose distribution scheme.

Figure 3:
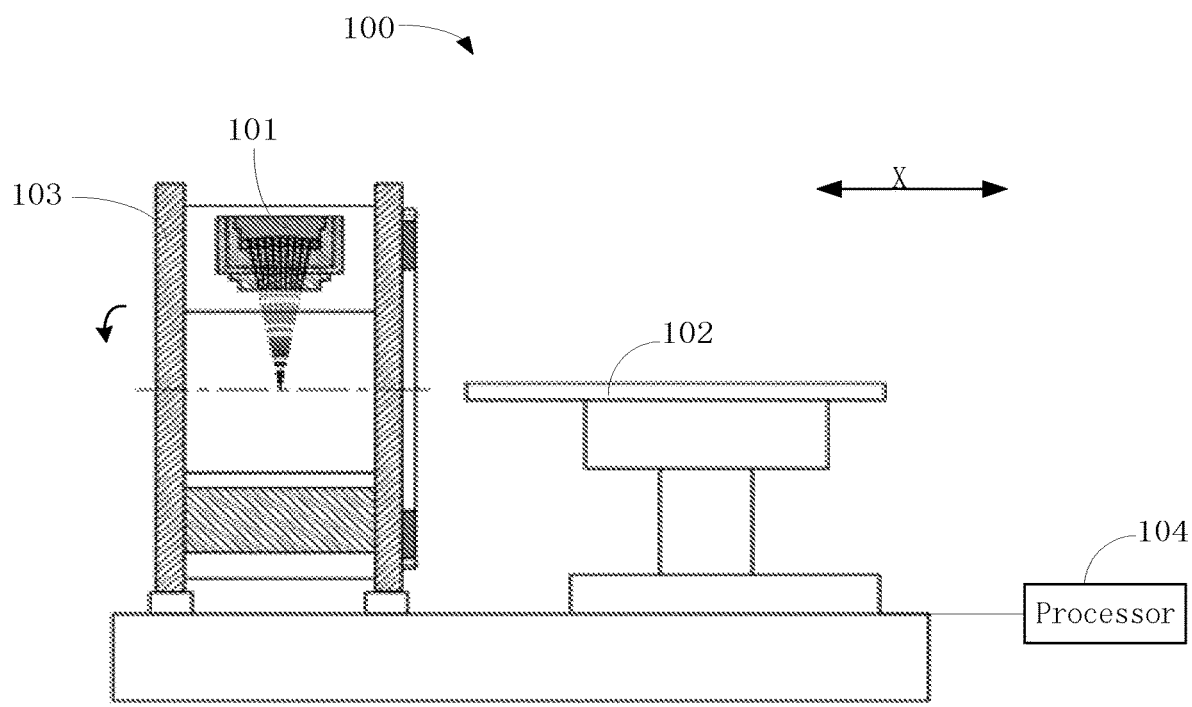
FIG. 3 is a schematic diagram of a radiotherapy system, according to one exemplary embodiment.

Referring to FIG. 3, the present disclosure further provides a radiotherapy system 100 including the above-described treatment planning apparatus 10. The radiotherapy system 100 includes at least one therapeutic head 101, a treatment couch 102, a rotatable gantry 103, e.g. in cylinder shape, and a processor. The therapeutic head 101 is used to generate radiation beams, the treatment couch 102 is used to position the target region (patient's lesion), and the rotatable gantry 103 is used to support the at least one therapeutic head 101 and continuously drive the therapeutic head 101 moving in multiple dimensions with respect to the treatment couch 102. The processor is used to perform actions of the mentioned various modules. The at least one therapeutic head 101 is continuously moved in at least one dimension relative to the target region such that the radiation angle is continuously variable.

In this embodiment, the at least one therapeutic head 101 is disposed on the rotatable gantry 103. The therapeutic head 101 follows the rotatable gantry 103 to continuously rotate around the target region, and results a rotational movement about a central axis (x axis) of the rotatable gantry 103. In this embodiment, the therapeutic head 101 may be a conformal therapeutic head 101 or a focused therapeutic head 101.

Figure 4:
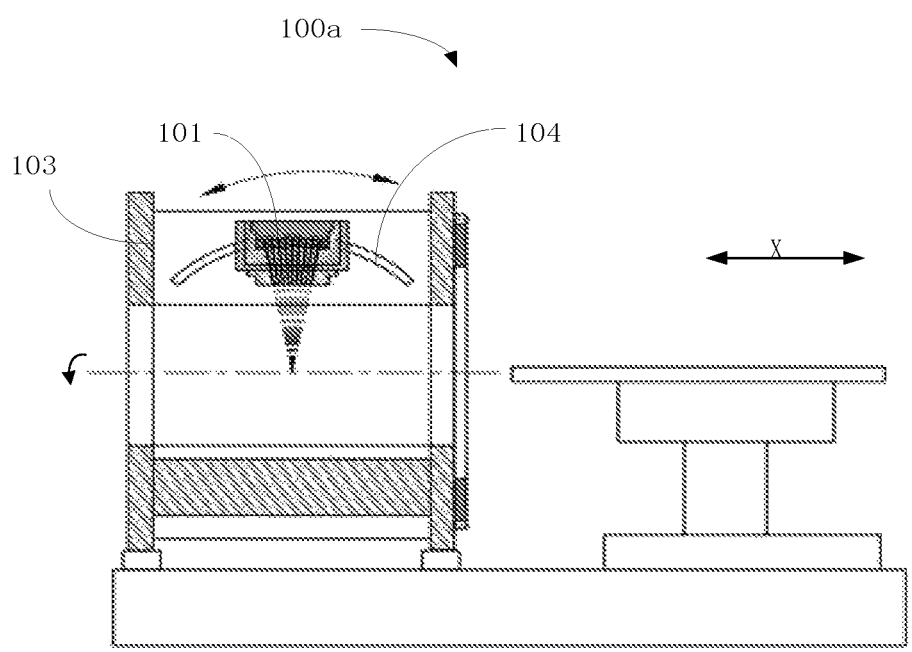
FIG. 4 is a schematic diagram of a radiotherapy system, according to another exemplary embodiment.

Referring to FIG. 4, in another embodiment, the radiotherapy system 100a further includes an arc-shaped guide rail 104 disposed on the inner side wall of the rotatable gantry 103. The arc-shaped guide rail 104 is disposed in a direction along the central axis of the gantry 103. At least one of the therapeutic heads 101 is disposed on the arc-shaped guide rail 104, thus the therapeutic head 101 also swings along the arc-shaped guide rail 104 in the direction of the central axis while continuously following the rotation movement of the gantry 103.

In the present disclosure, the therapeutic head is rotatable along the central axis of the gantry, and the direction of the rotation movement is defined as a first dimension to the movement of the therapeutic head. The therapeutic head also moves along the direction of the central axis, which is defined as a second dimension to the movement of the therapeutic head. In the present embodiment, the dose distribution at different radiation angles is defined as the dose distribution of the therapeutic head at different angles in the second dimension.

Figure 5:
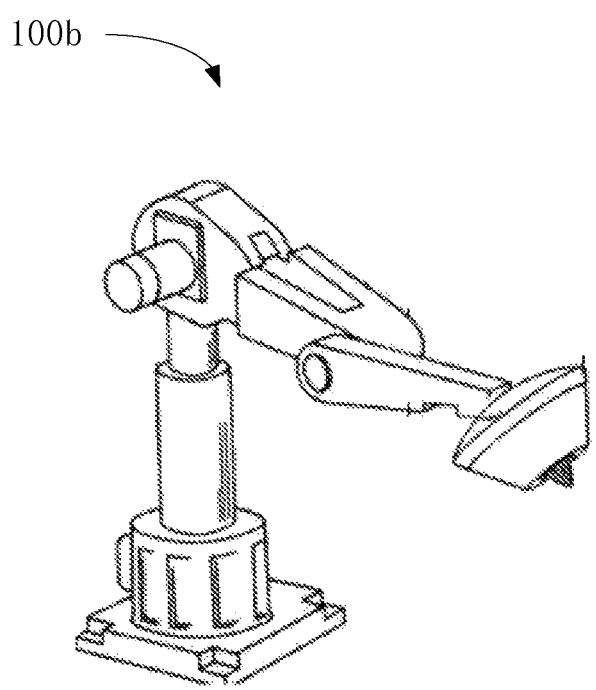
FIG. 5 is a schematic diagram of a radiotherapy system, according to another exemplary embodiment.

Referring to FIG. 5, in another embodiment, the radiotherapy system 100b may achieve multi-dimension options for radiation angle and radiation distance through a multi-joint robotic control.

It can be understood that in other embodiments, the therapeutic head of the radiotherapy system 100 may be set to move in multiple dimensions in various ways according to actual needs. In addition, in order to increase the treatment efficiency and the dose adjustment flexibility, the number of the therapeutic heads may also be increased to three or more according to actual needs. Accordingly, the preset algorithm function is also adjusted.

A number of embodiments will be specified below to illustrate the treatment planning process of the radiotherapy system 100 described above.

Figure 6:
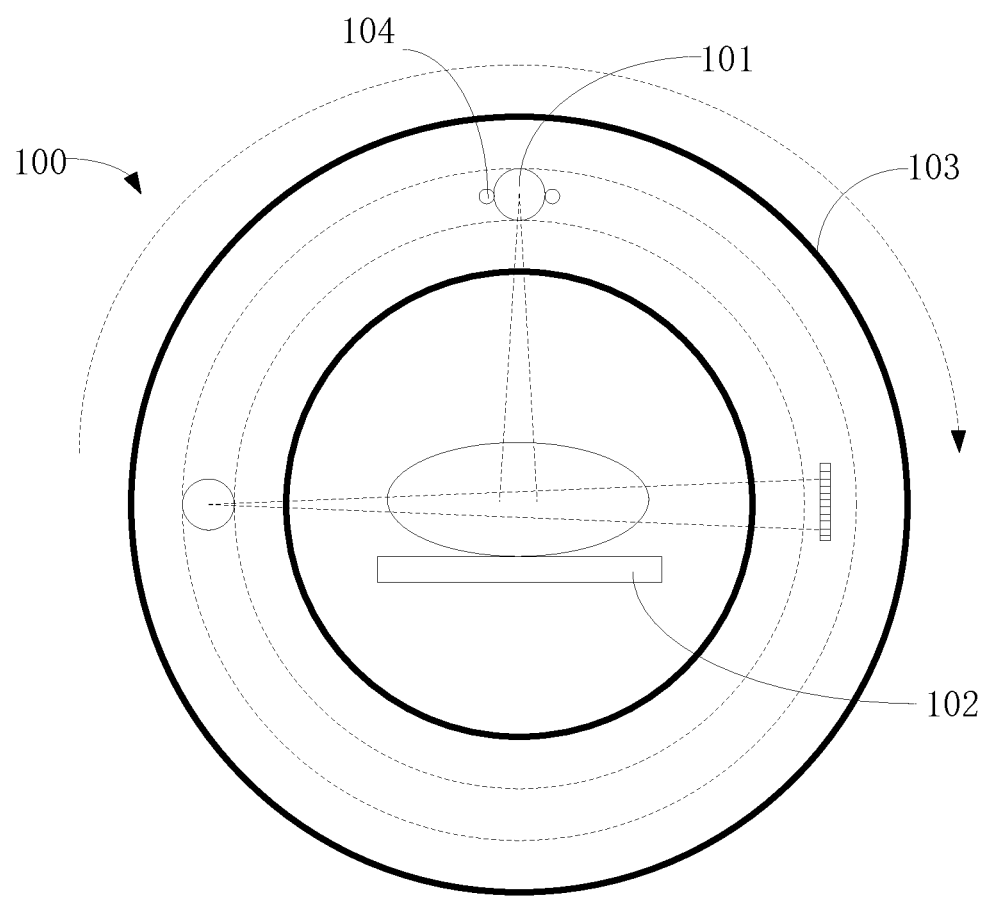
FIG. 6 is a schematic diagram of a radiotherapy system, according to another exemplary embodiment.

Referring FIG. 6, in another embodiment, the radiotherapy system 100 includes a conformal therapeutic head 101 with single radioactive source, and capable of continuously moving along the rotatable gantry 103 and/or the arc-shaped guide rail 104. In this case, the preset algorithm includes a function of:

$$S = \sum_{i=1}^{n} \{f(\Phi_i, \theta_i, B, D_i, t_i, d_i)\}$$

Wherein, S is an accumulative or superimposed dose distribution on the target region, and n is the number of times of position changing of the radioactive source.

In the step S102, different variables Φi, ti, Di, ti, di and fixed B values are respectively substituted to the function to obtain a plurality of S values, and the calculated multiple S values are respectively compared to that of the preset radiation dose scheme, to determine the respective dose distribution parameters that are closest to the preset radiation dose and the treatment plan is then determined.

Figure 7:
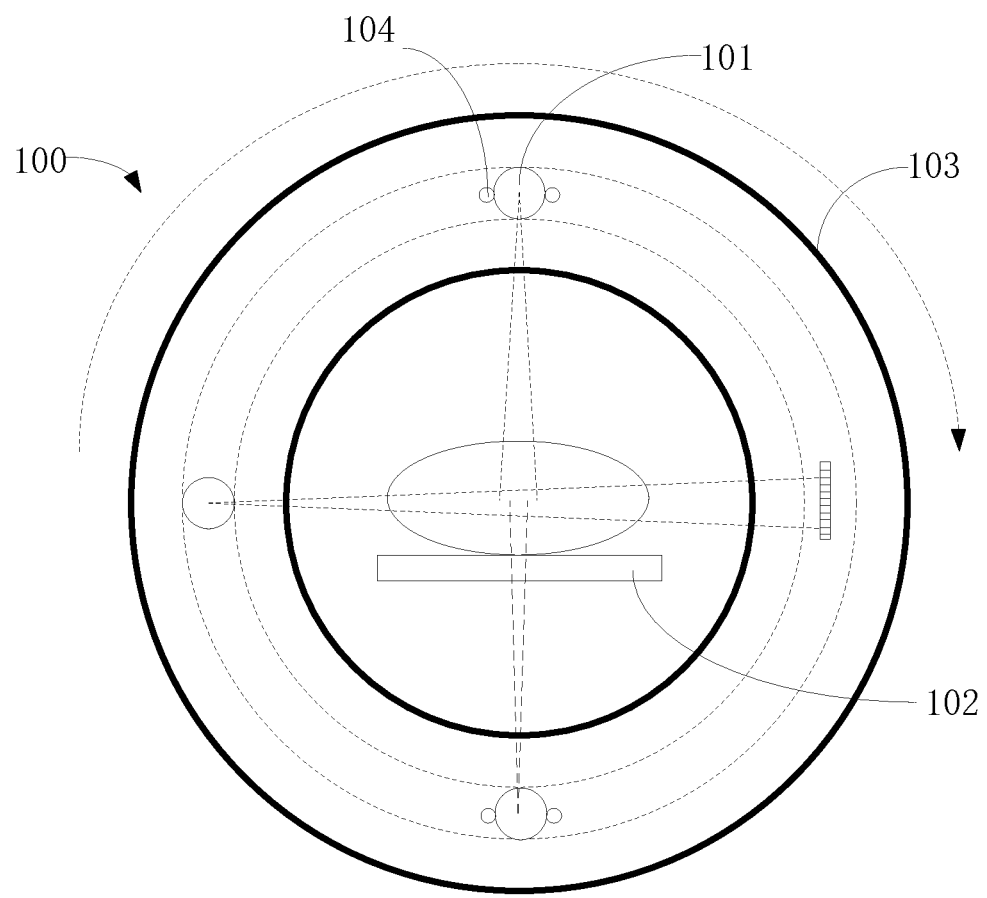
FIG. 7 is a schematic diagram of a radiotherapy system, according to another exemplary embodiment.

Referring to FIG. 7, in another embodiment, the radiotherapy system 100 includes more than two conformal therapeutic heads 101, and the conformal therapeutic heads 101 are all disposed and movable on the same rotatable gantry 103 and/or corresponding arc-shaped guide rail 104. In this case, the preset algorithm is adjusted to include a function of:

$$\S_1 = \sum_{i=1}^{p} \left\{ \sum_{i=1}^{n} \{f(\Phi_i, \theta_i, B, D_i, t_i, d_i)\} \right\}$$

Wherein, § h is an accumulative or superimposed dose distribution on the target region, and q represents the number of the conformal therapeutic heads 101.

In the step S102, different variables Φi, ti, Di, ti, di and fixed B values are respectively substituted to the function to obtain a plurality of § 1 values, and the calculated multiple § 1 values are respectively compared to that of the preset radiation dose scheme, to determine the respective dose distribution parameters that are closest to the preset radiation dose and the treatment plan is then determined.

Figure 8:
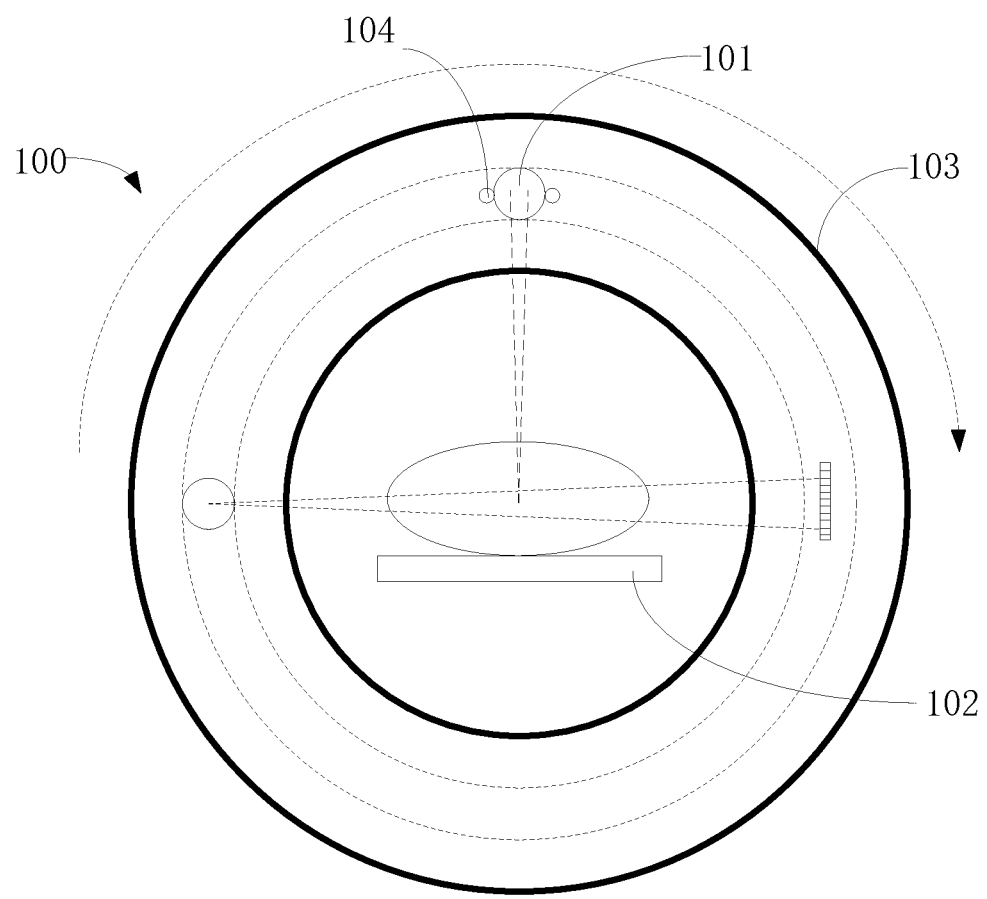
FIG. 8 is a schematic diagram of a radiotherapy system, according to another exemplary embodiment.

Referring to FIG. 8, in another embodiment, the therapeutic head 101 includes a single focused therapeutic head 101 comprising a plurality of radioactive sources, and the focused therapeutic head 101 may continue to move along the rotatable gantry 103 and/or the arc-shaped guide rail 104. In this case, the preset algorithm is adjusted to include a function of:

$$\S_2 = \sum_{i=1}^{o} \left\{ \sum_{i=1}^{m} \{f(\Phi_i, \theta_i, B, D_i, t_i, d_i)\} \right\}$$

Wherein, § 2 is an accumulative or superimposed dose distribution on the target region, o is the number of times of position changing of the focused therapeutic head 101, and m represents the number of the radioactive sources.

In the step S102, different variables of Φi, ti, Di, ti, di and fixed B are respectively substituted to the function to calculate a plurality of § 2 values, and the calculated plurality of § 2 values are respectively compared to that of the preset radiation dose scheme, to determine the dose distribution parameters that are closest to the preset radiation dose and the treatment plan is then determined.

Figure 9:
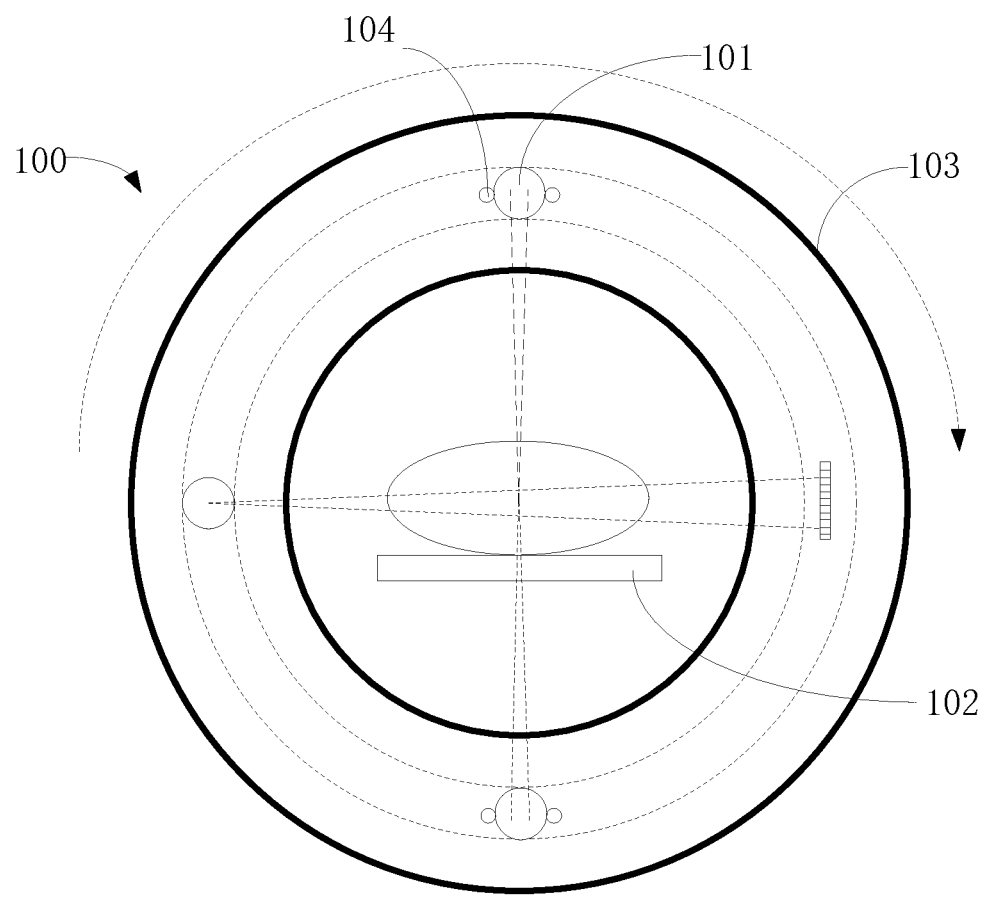
FIG. 9 is a schematic diagram of a radiotherapy system, according to another exemplary embodiment.

Referring to FIG. 9, in another embodiment, the number of the focused therapeutic heads 101 in the radiotherapy system 100 is more than two, and both are disposed on the same rotatable gantry 103 and/or arc-shaped guide rail 104 to continuously move. For this case, the preset algorithm is adjusted to include a function of:

$$\S_3 = \sum_{i=1}^{q} \left\{ \sum_{i=1}^{o} \left\{ \sum_{i=1}^{m} \{f(\Phi_i, \theta_i, B, D_i, t_i, d_i)\} \right\} \right\}$$

Wherein, 3 is a superimposed or accumulative dose distribution on the target region, q represents the number of the focused therapeutic heads 101.

In the step S102, different variables of Φi, ti, Di, ti, di and fixed B are respectively substituted to the function to calculate a plurality of § 3 values, and the calculated plurality of § 3 values are respectively compared to that of the preset radiation dose scheme, to determine the dose distribution parameters that are closest to the preset radiation dose and the treatment plan is then determined.

Figure 10:
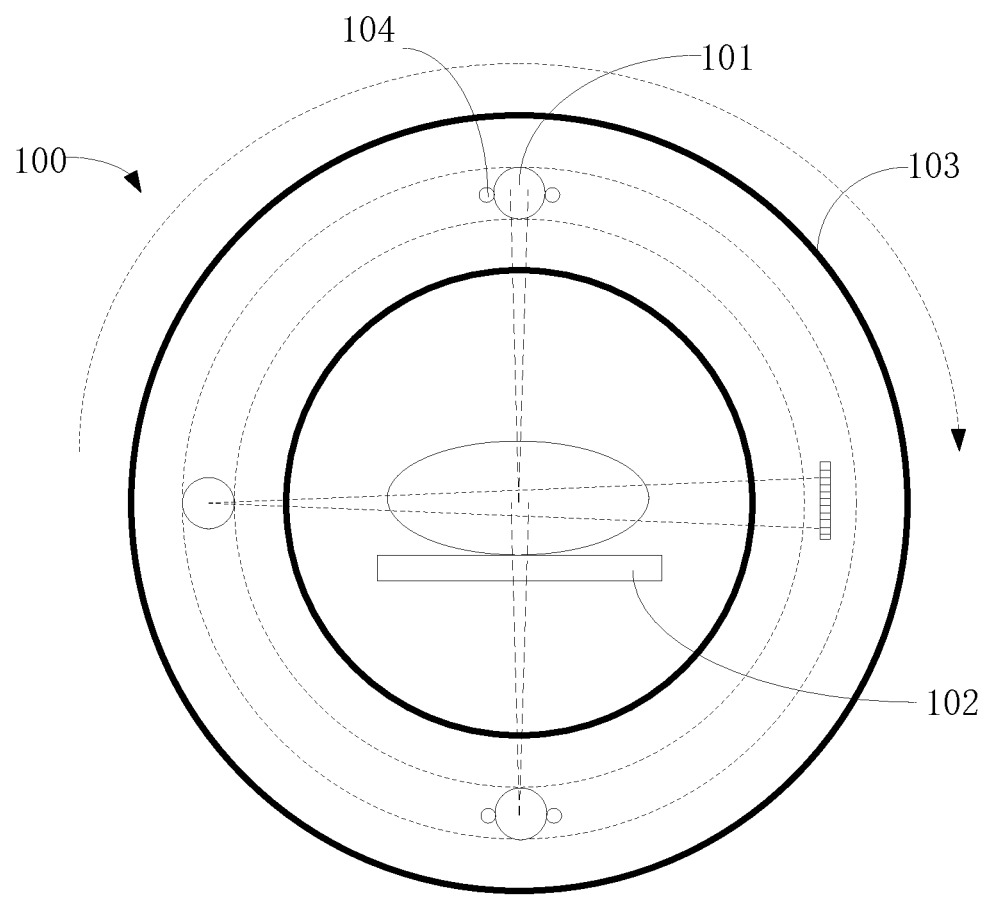
FIG. 10 is a schematic diagram of a radiotherapy system, according to another exemplary embodiment.

Referring to FIG. 10, in another embodiment, the radiotherapy system 100 includes at least one focused therapeutic head 101 and at least one conformal therapeutic head 101, and the focused therapeutic head 101 and the conformal therapeutic head 101 are all disposed on the same rotatable gantry 103, and/or respectively disposed on the corresponding arc-shaped guide rail 104, and capable of continuous movement. For this case, the preset algorithm is adjusted to include a function of:

$$\S = \S_1 + \S_3 = \sum_{i=1}^{p} \{S_{1i}\} + \sum_{i=1}^{q} \{S_{2i}\} = \sum_{i=1}^{p} \left\{ \sum_{i=1}^{n} \{f(\Phi_i, \theta_i, B, D_i, t_i, d_i)\} \right\} +$$
$$\sum_{i=1}^{q} \left\{ \sum_{i=1}^{o} \left\{ \sum_{i=1}^{m} \{f(\Phi_i, \theta_i, B, D_i, t_i, d_i)\} \right\} \right\}$$

Wherein, u1 is a superimposed or accumulative dose distribution of the conformal therapeutic head 101, § 3 is the superimposed or accumulative dose distribution of the focused therapeutic head 101, p represents the number of the conformal therapeutic heads 101, and n represents the number of times of the positional change of the radioactive source of the conformal therapeutic head, q represents the number of focused therapeutic heads 101, o represents the number of times of positional change of the focused therapeutic head 101, and m represents the number of radioactive sources in the focused therapeutic head.

In the step S102, different variables of Φi, ti, Di, ti, di and fixed B values are respectively substituted to the function to calculate a plurality of § values, and the calculated plurality of § values are respectively compared to that of the preset radiation dose scheme, to determine the respective dose distribution parameters that are closest to the preset radiation dose and the treatment plan is then determined. By this way, in addition to the performance of multi-angle radiation, the predetermined dose distribution may be more flexibly realized since the two therapeutic heads 101 cooperate, and the treatment efficiency is improved by more than double.

According to the treatment planning method of the present disclosure, the therapeutic head is located at different radiation angles by utilizing the continuous movement of the therapeutic head 101 (including rotation and swing movements, etc.), and the dose distribution of the therapeutic head is different at different radiation angles, so that the dose distribution schemes are adjustable by changing the radiation angle of therapeutic head(s). The adjusted dose distribution schemes are compared to the preset dose distribution scheme to obtain at least one radiation dose distribution scheme that is closest to the preset dose distribution scheme and further develops a treatment plan. As a result, the treatment planning accuracy is improved without changing the hardware configuration.

The foregoing descriptions are merely embodiments of the present disclosure, and do not limit the scope of the present disclosure. Any equivalent structure or equivalent process transformation using the description of the present disclosure and the accompanying drawings are directly or indirectly applied to other related technologies shall fall within the protection scope of the present disclosure.

What is claimed is:

1. A method of making a treatment plan with a treatment planning system, the treatment plan being applicable to a radiotherapy system, the method comprising:

acquiring a preset dose distribution scheme;

generating at least one radiation dose distribution scheme to be used with the treatment planning system, wherein the treatment plan system is generated based on at least one of beam energy of the radiotherapy system, a size of a collimator of the radiotherapy system, a radiation angle and radiation time of the radiotherapy system; and comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan, wherein the treatment planning system includes a preset algorithm, the preset algorithm generates the at least one radiation dose distribution scheme to be used based on a function of $f(\Phi, \theta, B, D, t, d)$, wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

2. The method according to claim 1, wherein the therapeutic head comprises a conformal therapeutic head with a single radioactive source, and the function of $f(\Phi, \theta, B, D, t, d)$ included in the preset algorithm comprises:

$$S = \sum_{i=1}^{n} \{f(\Phi_i, \theta_i, B, D_i, t_i, d_i)\}$$

wherein S is an indication of an accumulative dose distribution on the target region and n is an indication of a number of times of position changes of the radioactive source.

3. The method according to claim 2, wherein the therapeutic head comprises more than two conformal therapeutic heads, and the conformal therapeutic heads are all disposed and movable on a same rotatable gantry, and the function of $f(\Phi, \theta, B, D, t, d)$ included in the preset algorithm comprises:

$$\S_1 = \sum_{i=1}^{p} \left\{ \sum_{i=1}^{n} \{f(\Phi_i, \theta_i, B, D_i, t_i, d_i)\} \right\}$$

wherein, § 1 is an accumulative dose distribution on the target region, p is an indication of a number of the conformal therapeutic heads.

4. The method according to claim 1, wherein the therapeutic head includes a single focused therapeutic head comprising a plurality of radioactive sources, the focused therapeutic head is configured to continue to move with a rotatable gantry, and the function of $f(\Phi, \theta, B, D, t, d)$ included in the preset algorithm comprises:

$$\S_2 = \sum_{i=1}^{o} \left\{ \sum_{i=1}^{m} \{f(\Phi_i, \theta_i, B, D_i, t_i, d_i)\} \right\}$$

wherein § 2 is an accumulative dose distribution on the target region, o is a number of times of position changes of the focused therapeutic head, and m is an indication of a number of the radioactive sources.

5. The method according to claim 1, wherein the therapeutic head comprises at least two focused therapeutic heads, the at least two focused therapeutic heads are disposed on a same rotatable gantry, and the function of $f(\Phi, \theta, B, D, t, d)$ included in the preset algorithm comprises:

$$\S_3 = \sum_{i=1}^{q} \left\{ \sum_{i=1}^{o} \left\{ \sum_{i=1}^{m} \{f(\Phi_i, \theta_i, B, D_i, t_i, d_i)\} \right\} \right\}$$

wherein § 3 is an accumulative dose distribution on the target region, q is an indication of a number of the focused therapeutic heads.

6. The method according to claim 1, wherein the therapeutic head comprises at least one focused therapeutic head and at least one conformal therapeutic head which are all disposed on a same rotatable gantry for continuous movement, and the function of $f(\Phi, \theta, B, D, t, d)$ included in the preset algorithm comprises:

$$\S = \S_1 + \S_3 = \sum_{i=1}^{p}\{S_{1i}\} + \sum_{i=1}^{q}\{S_{2i}\} = \sum_{i=1}^{p}\left\{\sum_{i=1}^{n}\{f(\Phi_i, \theta_i, B, D_i, t_i, d_i)\}\right\} + \sum_{i=1}^{q}\left\{\sum_{i=1}^{o}\left\{\sum_{i=1}^{m}\{f(\Phi_i, \theta_i, B, D_i, t_i, d_i)\}\right\}\right\},$$

wherein § 1 is an accumulative dose distribution of the conformal therapeutic head, § 3 is an accumulative dose distribution of the focused therapeutic head, p is an indication of a number of the conformal therapeutic head, and n is an indication of a number of times of positional change of the radioactive source in the conformal therapeutic head, q is an indication of a number of the focused therapeutic head, o is an indication of a number of times of positional change of the focused therapeutic head, and m is an indication of a number of a radioactive sources in the focused therapeutic head.

7. The method according to claim 1, wherein the radiation field parameters of the therapeutic head are determined by a collimator of the therapeutic head, and when the collimator is an aperture collimator, the collimator includes a plurality of collimation holes, and the radiation field parameters are the sizes of the collimation holes; or, when the collimator is a multi-leaf collimator, the radiation field parameters are related to a shaped region through which radiation beams that is generated by the therapeutic head passes, wherein the shaped region is shaped by leaves of the collimator.

8. The method according to claim 1, wherein the therapeutic head is rotatable along a central axis of a rotatable gantry, and the first dimension is defined to be a direction of rotation movement of the therapeutic head.

9. The method according to claim 1, wherein the therapeutic head is moveable along a central axis of a rotatable gantry, and a second dimension is defined to be along a direction of the central axis.

10. The method according to claim 9, wherein the plurality of radiation dose distribution schemes are generated based on different radiation angles of the therapeutic head with respect to the target region in the second dimension.

11. The method according to claim 1, wherein at least one variable in the function of $f(\Phi, \theta, B, D, t, d)$ is zero.

12. The method according to claim 1, wherein the preset dose distribution scheme is calculated with semi-empirical model or Boltzmann transport equation.

13. The method according to claim 1, wherein the radiation angle is variable.

14. The method according to claim 1, wherein the comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan comprises:

comparing the at least one radiation dose distribution scheme to be used with the preset dose distribution scheme;

when a difference between the at least one radiation dose distribution scheme to be used and the preset dose distribution scheme is greater than a safety threshold, adjusting a parameter of the treatment planning system to regenerate the at least one radiation dose distribution scheme to be used;

comparing the at least one regenerated radiation dose distribution scheme to be used with the preset dose distribution scheme, and determining, among the at least one regenerated radiation dose distribution scheme, a radiation dose distribution scheme that is the closest to the preset dose distribution scheme to make the treatment plan.

15. The method according to claim 1, wherein the comparing the at least one radiation dose distribution scheme to be used with the preset dose distribution scheme, and determining, among the at least one radiation dose distribution scheme, a radiation dose distribution scheme that is the closest to the preset dose distribution scheme to make the treatment plan comprises:

comparing a difference between the at least one radiation dose distribution scheme to be used and the preset dose distribution scheme with a safety threshold, and determining a radiation dose distribution scheme to be used based on a result of the comparison to make the treatment plan.

16. A radiotherapy system, comprising:

at least one therapeutic head configured to generate a radiation beam;

a treatment couch configured to define a position of a target region;

a gantry configured to support the at least one therapeutic head, and move the therapeutic head relative to the treatment couch in multiple dimensions; and a treatment planning apparatus, the treatment planning apparatus including a processor, wherein the processor is configured with instructions to:

acquire a preset dose distribution scheme;

generate at least one radiation dose distribution scheme to be used, wherein the treatment plan is generated based on at least one of beam energy of the radiotherapy system, a size of a collimator of the radiotherapy system, a radiation angle and radiation time of the radiotherapy system; and compare the at least one radiation dose distribution scheme to be used with the preset dose distribution scheme, and determine, among the at least one radiation dose distribution scheme, a radiation dose distribution scheme that is the closest to the preset dose distribution scheme to make the treatment plan, wherein the treatment planning apparatus includes a preset algorithm, the preset algorithm generates the at least one radiation dose distribution scheme to be used based on a function of $f(\Phi, \theta, B, D, t, d)$, wherein the variable $\Phi$ is an indication of rotational angles of a therapeutic head of the radiotherapy system which is rotatable in a first dimension relative to the target region, the variable $\theta$ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

17. A method of making a treatment plan, the treatment plan being applicable to a radiotherapy system, the method comprising:

acquiring a preset dose distribution scheme;

generating a radiation dose distribution scheme to be used with a treatment planning system, wherein the treatment plan system is generated based on at least one of beam energy of the radiotherapy system, a size of a collimator of the radiotherapy system, a radiation angle and radiation time of the radiotherapy system such that a continuous change of radiation dose in a radiation region of the beam is formed with a specific spatial distribution; and comparing the radiation dose distribution scheme to be used with the preset dose distribution scheme, and determining a radiation dose distribution scheme that is the closest to the preset dose distribution scheme to make the treatment plan, wherein the treatment planning system includes a preset algorithm, the preset algorithm generates the at least one radiation dose distribution scheme to be used based on a function of f(Φ, θ, B, D, t, d), wherein the variable Φ is an indication of rotational angles of a therapeutic head of the radiotherapy system which is rotatable in a first dimension relative to the target region, the variable θ is an indication of swing angles of the therapeutic head relative to the target region in a second dimension, the second dimension is different from the first dimension, and B is an indication of beam energy of the radiotherapy system, the variable D is an indication of a distance from an emission point of a radioactive source of the therapeutic head to the target region, the variable t is an indication of radiation time, and the variable d is an indication of radiation field parameters of the therapeutic head of the radiotherapy system.

18. The method according to claim 17, wherein the therapeutic head comprises a conformal therapeutic head with a single radioactive source, and the function of f(Φ, θ, B, D, t, d) included in the preset algorithm comprises:

$$S = \sum_{i=1}^{n} \{f(\Phi_i, \theta_i, B, D_i, t_i, d_i)\}$$

wherein S is an indication of an accumulative dose distribution on the target region and n is an indication of a number of times of position changes of the radioactive source.

19. The method according to claim 17, wherein the therapeutic head includes a single focused therapeutic head comprising a plurality of radioactive sources, the focused therapeutic head is configured to continue to move with a rotatable gantry, and the function of f(Φ, θ, B, D, t, d) included in the preset algorithm comprises:

$$\S_2 = \sum_{i=1}^{o} \left\{ \sum_{i=1}^{m} \{f(\Phi_i, \theta_i, B, D_i, t_i, d_i)\} \right\}$$

wherein § 2 is an accumulative dose distribution on the target region, o is a number of times of position changes of the focused therapeutic head, and m is an indication of a number of the radioactive sources.

20. The method according to claim 17, wherein the therapeutic head comprises at least one focused therapeutic head and at least one conformal therapeutic head which are all disposed on a same rotatable gantry for continuous movement, and the function of f(Φ, θ, B, D, t, d) included in the preset algorithm comprises:

$$\S = \S_1 + \S_3 = \sum_{i=1}^{p} \{S_{1i}\} + \sum_{i=1}^{q} \{S_{2i}\} = \sum_{i=1}^{p} \left\{ \sum_{i=1}^{n} \{f(\Phi_i, \theta_i, B, D_i, t_i, d_i)\} \right\} + \sum_{i=1}^{q} \left\{ \sum_{i=1}^{o} \left\{ \sum_{i=1}^{m} \{f(\Phi_i, \theta_i, B, D_i, t_i, d_i)\} \right\} \right\},$$

wherein § 1 is an accumulative dose distribution of the conformal therapeutic head, § 3 is an accumulative dose distribution of the focused therapeutic head, p is an indication of a number of the conformal therapeutic head, and n is an indication of a number of times of positional change of the radioactive source in the conformal therapeutic head, q is an indication of a number of the focused therapeutic head, o is an indication of a number of times of positional change of the focused therapeutic head, and m is an indication of a number of a radioactive sources in the focused therapeutic head.

* * * * *